US00PP20900P2

(12) United States Plant Patent
Kelly et al.

(10) Patent No.: US PP20,900 P2
(45) Date of Patent: Mar. 30, 2010

(54) PIN OAK TREE NAMED 'PWJR08'

(50) Latin Name: *Quercus palustris*
Varietal Denomination: PWJR08

(76) Inventors: Joseph C. Kelly, 6511 NE. 41st St., Redmond, OR (US) 97756; Peter J. Brentano, 5009 Davidson Rd. NE., St. Paul, OR (US) 97137

( * ) Notice: Subject to any disclaimer, the term of this patent is extended or adjusted under 35 U.S.C. 154(b) by 0 days.

(21) Appl. No.: 12/315,680

(22) Filed: Dec. 4, 2008

(51) Int. Cl.
*A01H 5/00* (2006.01)

(52) U.S. Cl. ..... Plt./225

(58) Field of Classification Search ..... Plt./225
See application file for complete search history.

*Primary Examiner*—Susan B McCormick Ewoldt
(74) *Attorney, Agent, or Firm*—Klarquist Sparkman, LLP

(57) ABSTRACT

A new variety of *Quercus palustris* Pin Oak tree substantially as herein shown and described, characterized particularly by a combination of glossy foliage, new growth leaves that are pubescent, upright growth habit and orange-red Fall color.

8 Drawing Sheets

Latin name of genus and species: *Quercus palustris.*
Variety denomination: 'PWJR08'.

BACKGROUND

The present invention relates to a new and distinct variety of *Quercus palustris,* which has been given the varietal name 'PWJR08'. One of the inventors discovered the new tree as a chance seedling growing in a cultivated area of a nursery in St. Paul, Oreg. The new tree was first asexually propagated at the direction of the other inventor. This cultivated area also contained other seedling oak trees. The new variety differed from these other seedling oak trees growing in this area by its glossy foliage, pubescent new growth, upright growth habit and orange-red fall color.

The parentage of this new tree is unknown, but it is definitely a Pin Oak type tree and the inventors are convinced it is a new variety of *Quercus palustris.*

The original tree had been purchased as a 5–6 foot, bare root whip liner in the spring of 1992, and at that time was planted in a cultivated liner field of a nursery. This tree had grown from a seed. Having recognized this tree as unique, one of the inventors transplanted the tree to a landscape setting adjacent to the inventor's front yard at St. Paul, Oreg. in the spring of 1999, where it has remained since that time. It is now about 19 years old.

The description of this new Oak variety is based on observations of this original tree and of asexually propagated progeny, asexually propagated at and being grown at a nursery in Canby, Oreg.

BRIEF SUMMARY OF THE INVENTION

As the original tree of the new variety was observed, the uniqueness of this tree became apparent because of its unique branching habit, ascending growth habit, glossy summer foliage, pubescent new growth and orange-red fall color. These characteristics distinguish our new tree from other *Quercus palustris* Pin Oaks of which we are aware, such as *Quercus palustris* 'Pringreen' (U.S. Plant Pat. No. 9,093) and *Quercus palustris* 'Sovereign' (not patented).

The new variety was asexually propagated by chip budding in 2000 at the direction of one of the inventors, in Canby, Oreg. The progeny have thus far proven to retain the unique branching habit, ascending growth habit, glossy summer foliage, pubescent new growth and orange-red fall color of the original tree, even as smaller plants. This propagation and observation of the resulting progeny have proven the characteristics of our new variety to be firmly fixed and reproduce true to type. Furthermore, these observations have confirmed to the inventors that the new variety represents a new and improved variety of *Quercus palustris* oak tree.

This unique tree differs from trees known to the inventors of the *Quercus palustris* species in its upright habit compared to a more pendulous habit typical of the species, pubescent new growth compared to non-pubescent new growth typical of the species, glossy foliage compared to matte foliage typical of the species, orange-red fall color compared to red fall color typical of the species and smaller acorns compared to the larger acorns typical of the species.

This unique tree differs from *Quercus palustris* 'Pringreen' in its broader, more pyramidal form compared to a more columnar or fastigate form of 'Pringreen', its pubescent new growth compared to non-pubescent new growth of 'Pringreen', its glossy foliage compared to matte foliage of 'Pringreen' and its orange-red fall color compared to the deeper red fall color of 'Pringreen'.

This unique tree differs from *Quercus palustris* 'Sovereign' in its pubescent new growth compared to non-pubescent new growth of 'Sovereign', its darker green foliage compared to lighter green foliage of 'Sovereign' and its orange-red fall color compared to the deeper red fall color of 'Sovereign'.

BRIEF DESCRIPTION OF THE DRAWINGS

The accompanying photographs depict the color of the tree and foliage of our new variety as nearly true as is reasonably possible to make the same in a color illustration of this character.

DETAILED BOTANICAL DESCRIPTION

Figure 1:
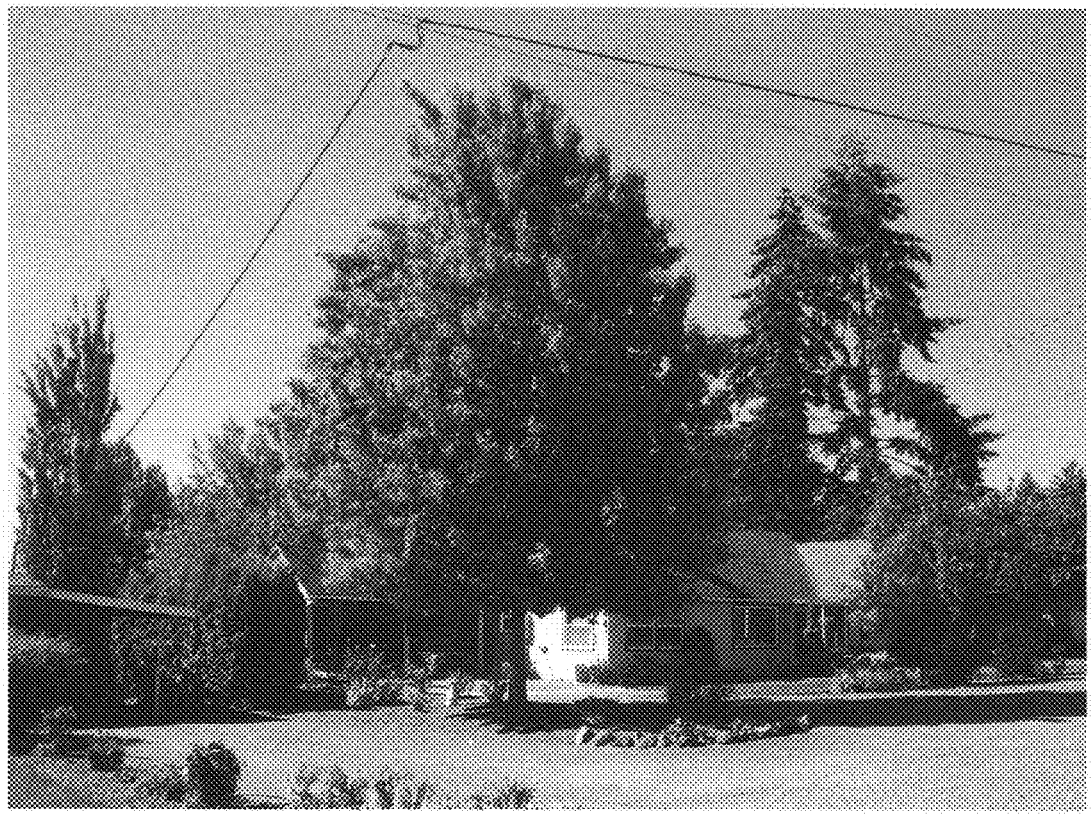
FIG. 1 is a photograph of the original tree of our new variety illustrating its upright growth habit.
Figure 2:
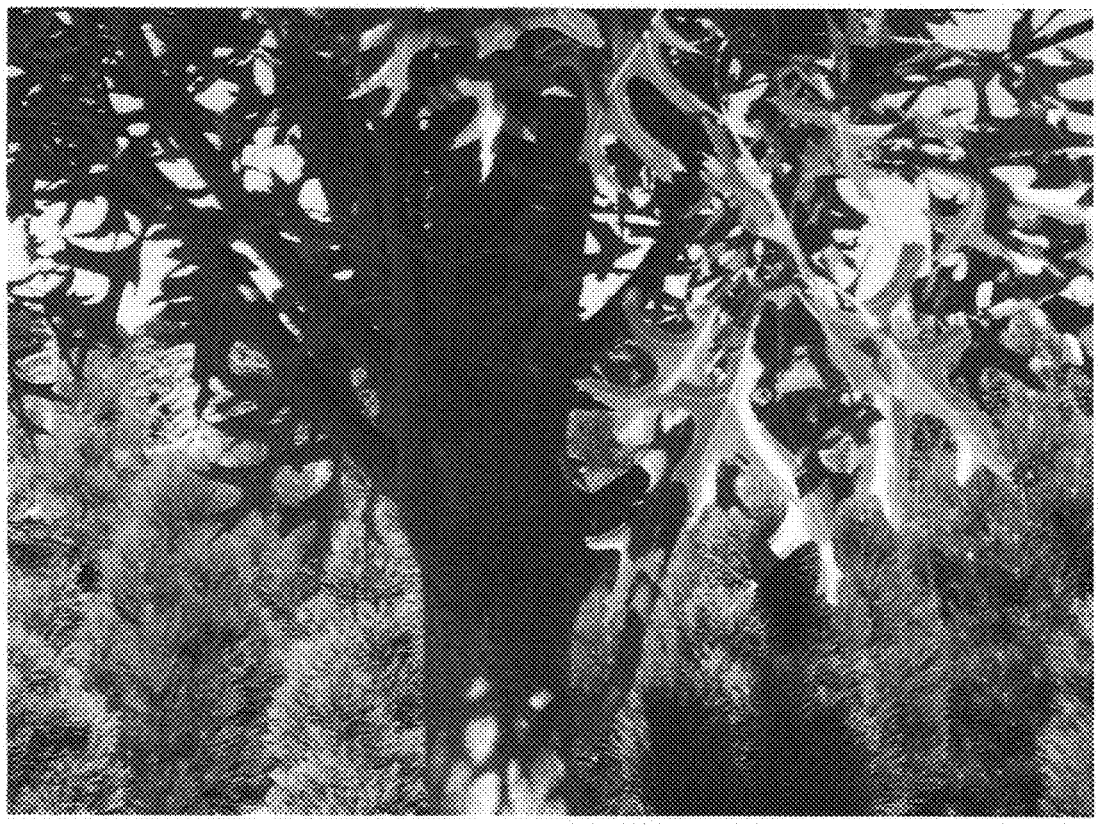
FIG. 2 is a close up photograph of a portion of a four year old tree of our new variety showing its upright and ascending branching habit.
Figure 3:
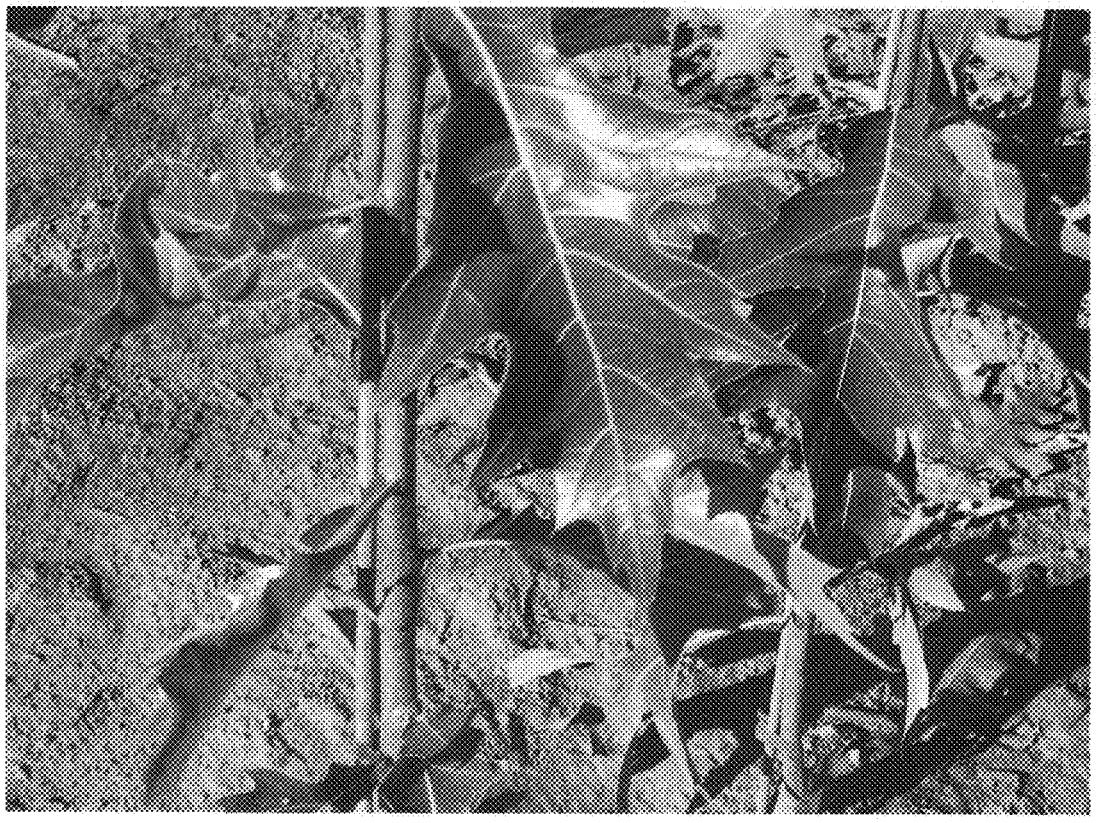
FIG. 3 is a close up of the upper surface of leaves of trees of our new variety showing the glossy characteristic of the foliage.
Figure 4:
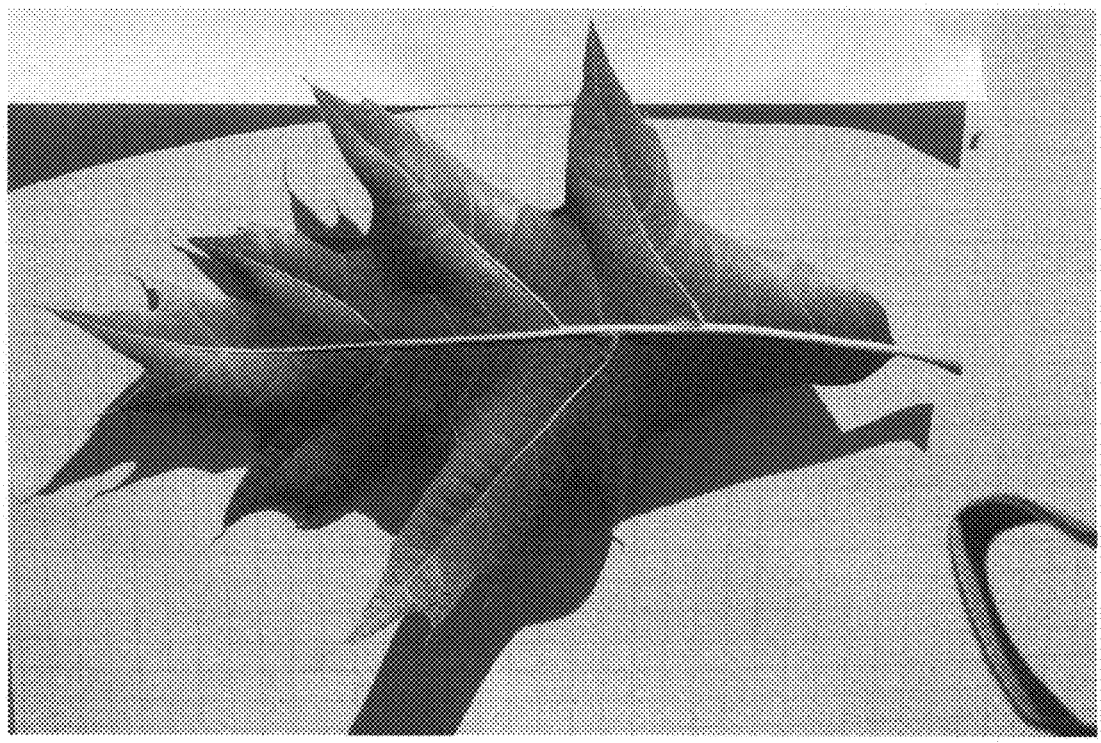
FIG. 4 is a photograph of the underside of a leaf of our new variety.
Figure 5:
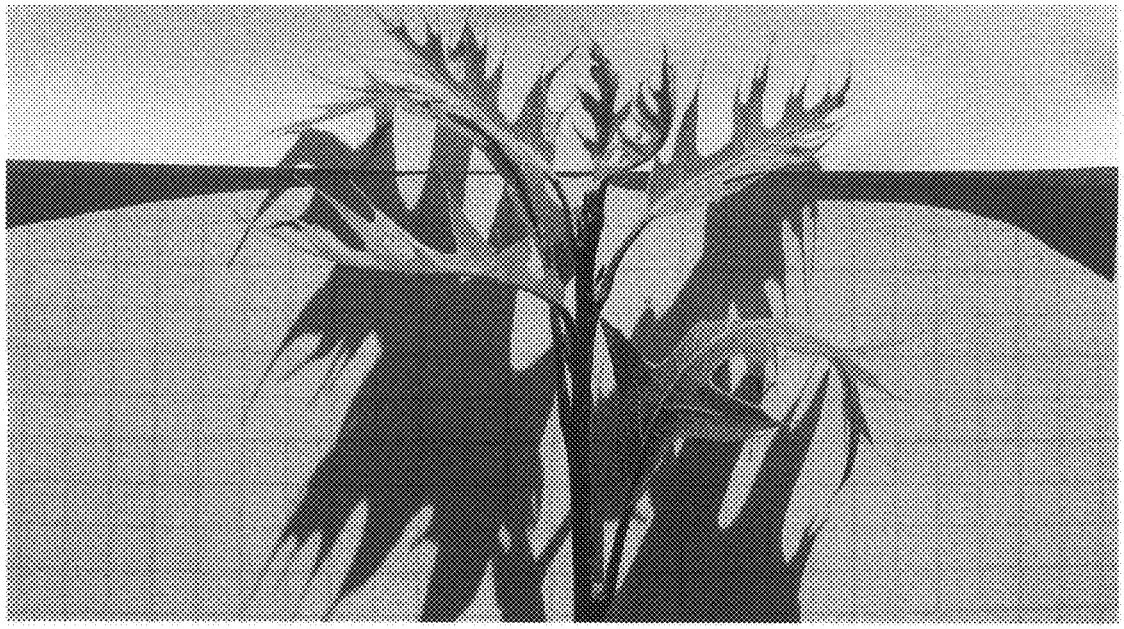
FIG. 5 is a close up of a portion of new growth leaves of our new variety, illustrating pubescence of the leaves.
Figure 6:
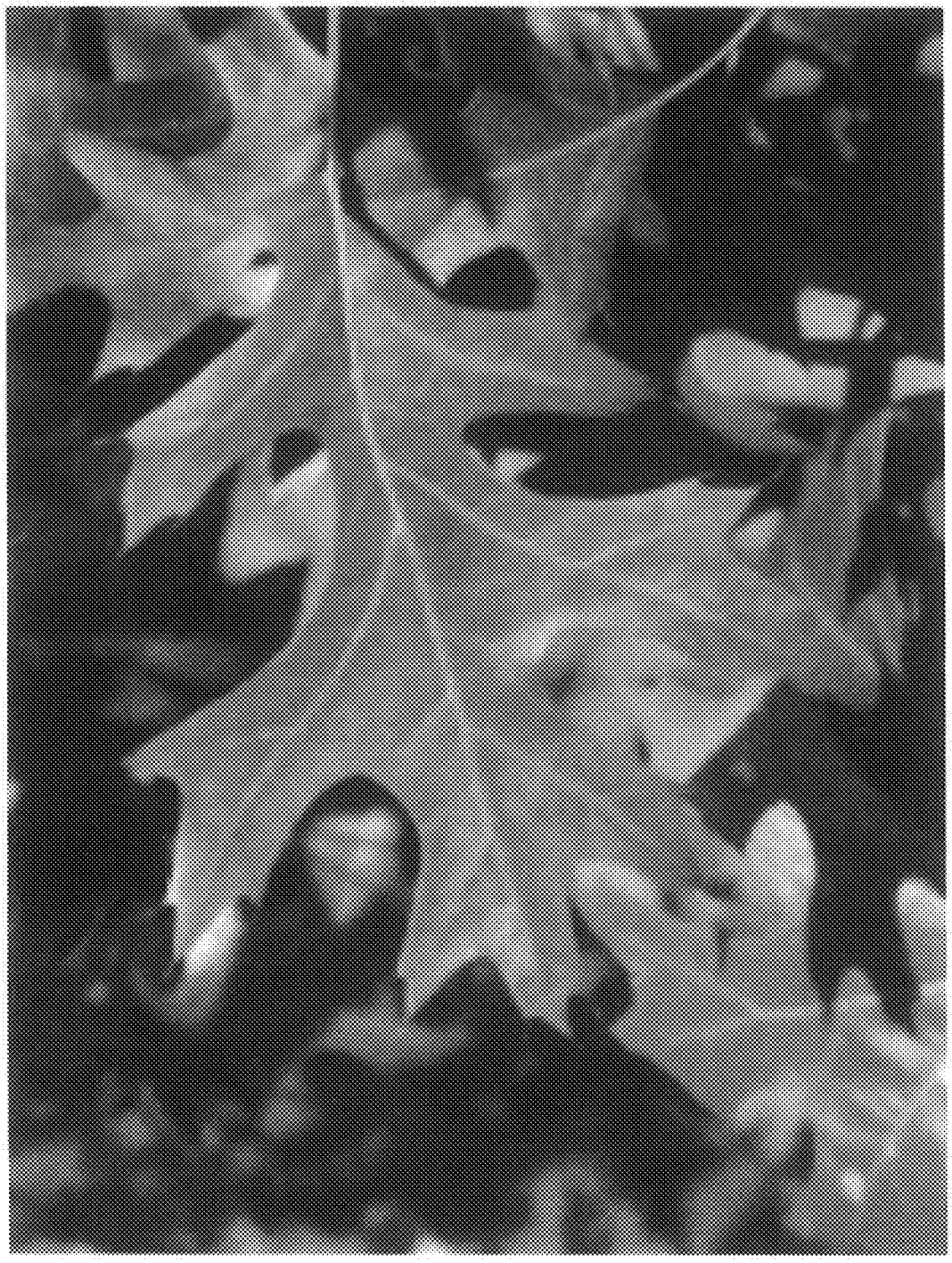
FIG. 6 is a photograph of leaves of our new variety in Fall color.
Figure 7:
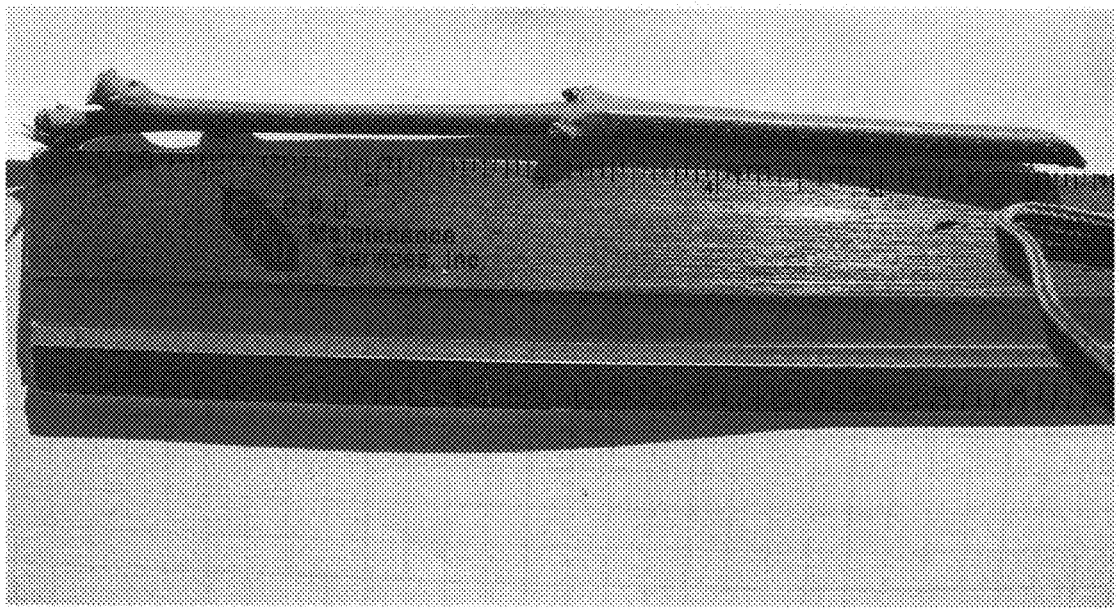
FIG. 7 is a photograph of a portion of a branch of a tree of our new variety.
Figure 8:
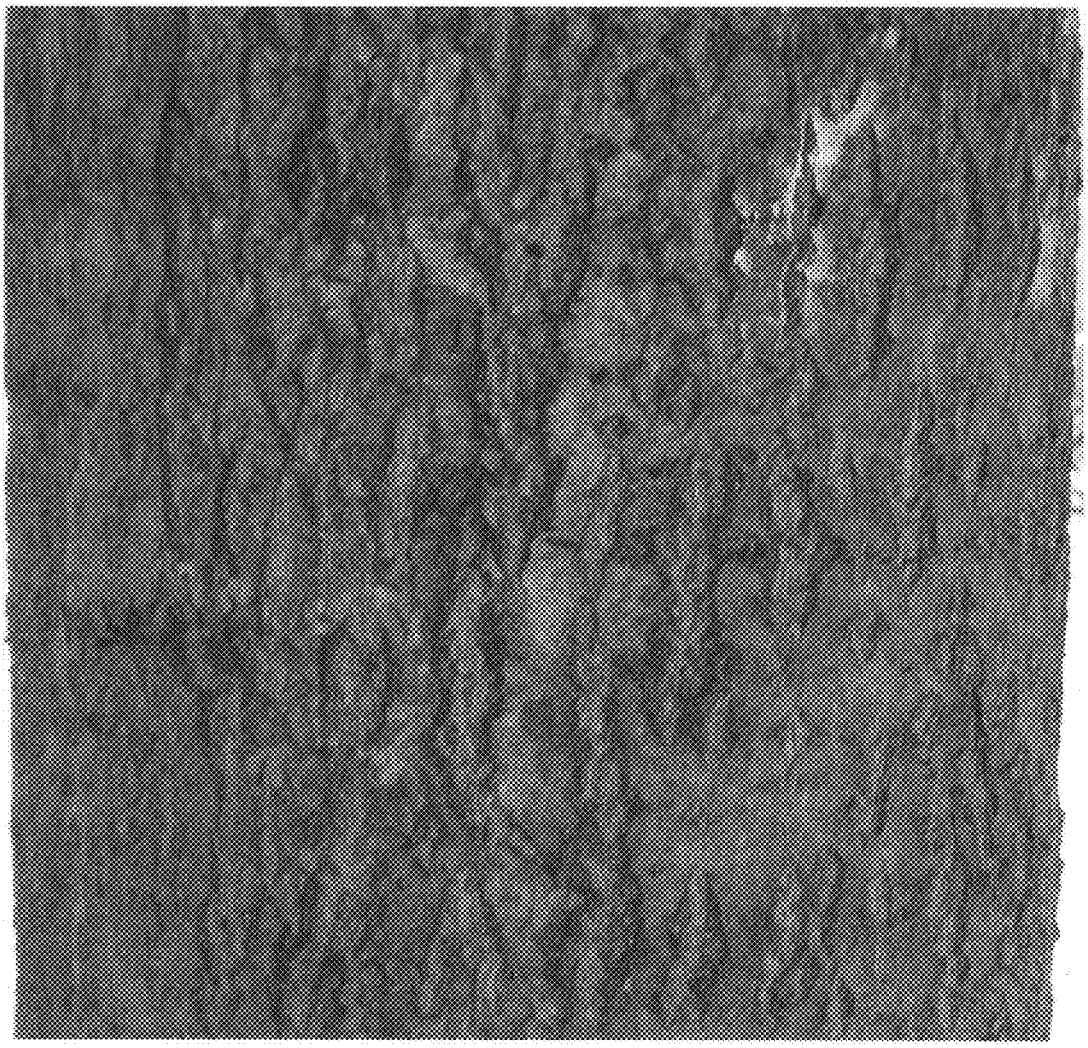
FIG. 8 is a photograph of the bark of the original tree of our new variety, illustrating the moderately ridged nature of the bark and the color of striations of the bark.

Our 'PWJR08' variety of Oak tree is currently growing at an observation site in St. Paul, Oreg. It is located in an area of Oregon that has a deep, alluvial, Qutama Loam soil type and receives approximately 40 inches of rain per year. Clackamas County, Oreg. is in USDA Hardiness Zone 8A.

Our new tree has not been observed under all growing conditions, and thus, variations may occur as a result of different growing conditions.

The following is a detailed description of our new variety of our new tree with color terminology in accordance with The Royal Horticultural Society (R.H.S.) Colour Chart, copyright 2001, published by The Royal Horticultural Society in London. The observations are of the original tree growing in the landscape setting at St. Paul, Oreg.; of 4 year old asexually propagated progeny growing at a nursery in St. Paul, Oreg.; and of a 2 year old asexually propagated progeny growing at a nursery in Canby, Oreg.

Parentage: Discovered as a chance seedling growing in a cultivated area of a nursery in St. Paul, Oreg. The parentage of this tree is believed be *Quercus palustris* (pollen parent) and *Quercus palustris* (seed parent).

Tree shape: Upright, broadly pyramidal canopy, with a central leader.

Trunk: The trunk is typical of the species with a strong central leader. At about age 2 yr., the initially discovered tree had a diameter of about ½ inches in diameter measured 6 inches above the ground.

Bark: Bark is smooth, and green in color (RHS 137C) on young trees. Mature bark is grey in color (RHS 198D) with striations of grey-brown (RHS 199D), becoming moderately ridged.

Trunk lenticels:

*Shape.*—Oval-elongated.

*Size.*—About 1/64 inch.

*Color.*—Grey-brown (RHS N163B).

*Leaf stomata.*—Shape: irregular. Size: 1/32 inch. Color: green (RHS 163B).

Size and growth rate: The original tree of our variety is currently eighteen and one-half inches in diameter at 54 inches above the ground with a similar caliper measurement at 6 inches above the ground, it is about 50 feet high, and about 35 feet wide, thus providing an overall height to width ratio of about one and one-half to one. Since transplanting to the observation site as a 4½ inch caliper transplant, the original tree has had an average growth in caliper of about 1½ inches per year and vegetative growth of approximately 36 inches per year.

Branching habit: Branching is upright and ascending with strong branch attachments. Primary branches emerge from the trunk at about a 35-degree angle to the leader.

Branches: Surface texture is smooth. Color is green (RHS 137C). Branch lenticels: On a branch having a 2 inch caliper, average branch lenticel size is about one-fourth inch. The lenticel shape is oval-elongated. Lenticel color is yellow-white (RHS 158C) to greyed-yellow (RHS 162C).

Foliage: The tree has leaves that are mostly typical of *Q. palustris.*

Shape: Alternate, simple, obovate to elliptic, 6 to 7 inches long, 3 to 4 inches wide, with one and one-quarter inch to one and one-half inch lobes. Sinuses are terminal, long and acuminate.

Color: Summer color of upper leaf surface is green and glossy (RHS N134C); summer color of lower leaf surface is yellow-green (RHS 145D). Fall color of upper leaf surface is orange-red (RHS 33A) to red (RHS 44A); fall color of lower leaf surface is purple-red (RHS 183A) to grey-red (RHS 180A). Spring color of upper leaf surface is green and glossy (RHS 134C); spring color of lower leaf surface is yellow-green (RHS 145C). Vein color is green (RHS 145A).

Pubescence: Location, upper and lower surface on new foliage; color yellow-green (RHS 145D).

Overall shape: Lobed.

Base: Cuneate.

Apex: Truncate.

Surface texture: Smooth, glossy.

Petiole: Average length approximately 2 inches to two and one-half inches. Diameter one-quarter inch to five-eighths inch. Surface texture is smooth-matte. Color is red-purple (RHS 61B).

Buds:

*Typical of the species, being imbricate, conical to ovate, size.*—One-sixteenth inch to one-quarter inch long.

*Diameter.*—One-quarter inch; color is grey-brown (RHS 199A) to grey-brown (RHS N199A), with ciliate scale margins.

Flowers: Typical of the species, monoecious. The staminate catkins are pendent and clustered. The individual flowers comprise a 5 to 6 lobed calyx that encloses 2 to 3 stamens. Pistillate flowers are: solitary or in 2 to 3 flowered spikes from the axils of the new leaves. Individual pistillate flowers consist of: a cup-shaped, lobed calyx surrounding the ovary, with the whole partly enclosed in an involucre.

Fruit: Acorns are atypical of species. Acorns are smaller than the species, oval and compressed; one-quarter inch to three-eights inch long; one-quarter inch to three-eighths inch in diameter; stock, short with a diameter of one-thirty second inch; length one-thirty second inch; approximately one-third of the acorn is covered by the cap. The acorn is green in color (RHS N138C). Striations: vertical; color: yellow-green (RHS 144C). The cap color is grey-brown (RHS 199C).

Root system: The root system is typical of the species being fibrous with a strong tap root development.

Pest and disease resistance: No pests or diseases have been observed. Tolerance to pH soil conditions is unknown.

Winter hardiness: Typical of the species at Zone 4A.

We claim:

1. A new variety of *Quercus palustris* Pin Oak tree substantially as herein shown and described, characterized particularly by a combination of glossy foliage, new growth leaves that are pubescent, upright growth habit and orange-red Fall color.

* * * * *